United States Patent [19]

Liebowitz et al.

[11] Patent Number: 5,916,594
[45] Date of Patent: Jun. 29, 1999

[54] PROCESS OF MAKING SOLID RIBAVIRIN DOSAGE FORMS

[75] Inventors: Stephen M. Liebowitz, Neshanic Station; Elliot I. Stupak, West Caldwell; Imtiaz A. Chaudry, North Caldwell; Winston A. Vadino, Whitehouse Station; Frank E. Bowen, Rutherford, all of N.J.

[73] Assignee: Schering Corporation

[21] Appl. No.: 08/997,169

[22] Filed: Dec. 22, 1997

[51] Int. Cl.[6] ................................. A61K 9/20; A61K 9/48
[52] U.S. Cl. ............................. 424/465; 424/452
[58] Field of Search ..................... 424/452, 465

[56] References Cited

U.S. PATENT DOCUMENTS

| | | | |
|---|---|---|---|
| 3,424,842 | 1/1969 | Nurnberg | 424/94 |
| 3,490,742 | 1/1970 | Nichols et al. | 252/99 |
| 3,622,677 | 11/1971 | Short et al. | 424/361 |
| 4,681,765 | 7/1987 | Guley | 424/456 |
| 4,886,669 | 12/1989 | Ventouras | 424/469 |
| 5,030,447 | 7/1991 | Joshi et al. | 424/80 |
| 5,370,878 | 12/1994 | Shah | 424/469 |
| 5,492,692 | 2/1996 | Digenis et al. | 424/78.25 |
| 5,506,248 | 4/1996 | Nikfar et al. | 514/374 |
| 5,605,889 | 2/1997 | Curatolu et al. | 424/464 |
| 5,738,872 | 4/1998 | Ortyl et al. | 424/452 |

FOREIGN PATENT DOCUMENTS

| | | |
|---|---|---|
| 346132 A1 | 12/1989 | European Pat. Off. . |
| 06298665 | 10/1994 | Japan . |
| 07165616 | 6/1995 | Japan . |

OTHER PUBLICATIONS

Prusiner et al Acta Crystallogr. B32(2):419–426 "Two Polymorphic Crystalline Forms of Virazole . . . ", (1976).

Prusiner et al Nature 244(134): 116–118 (Virazole, 2. Cryst. Polymorphs A & B), (1973).

Ding et al Zhongguo Linchuang Yaolixue Zazh1 10(3): 177–180 "Bioavailability of Ribavirin Capsules in Healthy Volunteers", (1994).

Magnussen et al Antimicrob. Agents Chemother. 12(4): 498–502 "Double Blind Evaluation of Oral Ribavirin (Virazole) in Exp. Influenza a Virus Infection in Volunteers", (1977).

Togo et al. Jl. Infect. Diseases 133 Suppl. A109–A103 Double Blind Clinical Assessment of Ribavirin (Virazole) in the Prevention of Induced Infection with Type B Influenza Virus, 1976.

*Primary Examiner*—Shep K. Rose
*Attorney, Agent, or Firm*—Thomas D. Hoffman

[57] ABSTRACT

A process of making an orally administrable solid dosage form containing a compacted ribavirin composition having an advantageously high tap density of at least 0.6 g/mL as well as surprisingly rapid disintegration and dissolution rates and wherein the ribavirin is substantially free of polymorphic forms of ribavirin as determined is disclosed.

11 Claims, No Drawings

PROCESS OF MAKING SOLID RIBAVIRIN DOSAGE FORMS

BACKGROUND OF THE INVENTION

This invention relates to a process of making orally administrable solid dosage forms comprising a compacted ribavirin composition having an advantageously high tap density as well as surprisingly fast disintegration and dissolution rates and containing a freely flowing ribavirin of uniform physical characteristics which is substantially free of other polymorphic forms.

Ribavirin is an antiviral agent which is currently being administered in association with interferon alpha-2b to treat patients with chronic hepatitis C infections.

Ribavirin 200 mg capsules are manufactured and marketed by ICN Pharmaceuticals in Canada under the trade name Virazole™ capsules. The ribavirin used to make the ribavirin composition in the Virazole capsules is a non-freely flowing powder with low and variable tap densities in the range of 0.320 to 0.449 g/mL. A ribavirin composition with a tap density of at least 0.6 g/mL is needed for the uniform filling of the 200 mg capsules. It would be desirable for the ribavirin composition to have a uniformly high tap density of at least 0.6 g/mL to fill any capsule and to avoid excessive weight variation and excessive packing in the capsule shell during the capsule filling operation especially in the high speed capsule filling equipment which operate at a fill rate of over 20,000 capsules per hour.

Dry compacting of the ribavirin formulation would be an attractive solution to this problem so long as the heat produced during the compaction operation does not cause the formation of ribavirin polymorphic forms, which forms are unacceptable for obtaining health registration.

The Virazole capsules exhibited inconsistency in meeting the dissolution specifications which requires that 80% of the ribavirin be dissolved in water in 30 minutes. The disintegration times of the Virazole composition were typically around 20 minutes.

There is a need for a ribavirin composition with a tap density of at least 0.6 g/mL and having improved dissolution rates and reduced disintegration times. There is also a need to compact the ribavirin composition to achieve such high tap densities while maintaining the ribavirin in the physical state substantially free of polymorphic forms.

SUMMARY OF THE INVENTION

The invention provides an orally administrable solid dosage form comprising a rapidly dissolving compacted ribavirin composition comprising ribavirin and a pharmaceutically acceptable disintegrant wherein said composition after dry compaction has a tap density of at least about 0.6 g/mL and wherein more than 80% by weight of the ribavirin dissolves in water in about 30 minutes.

The invention also provides a rapidly dissolving compacted ribavirin composition comprising:

(a) an antivirally effective amount of ribavirin;
(b) an effective amount of at least one filler selected from the group consisting of lactose anhydrous, lactose monohydrate, sucrose, mannitol, microcrystalline cellulose, pregelatinized starches, dibasic calcium phosphate dihydrate,calcium sulfate dihydrate and calcium sulfate trihydrate;
(c) an effective amount of a pharmaceutically acceptable disintegrant selected from the group consisting of croscarmellose sodium, sodium starch glycolate, corn starch, pregelatinized starches, sodium carboxymethyl cellulose, potato starch, microcrystalline cellulose, cross-linked polyvinylpyrrolidone,magnesium aluminium silicate, bentonite, alginic acid and alginates; and;
(d) an effective amount of a lubricant selected from the group consisting of magnesium stearate, calcium stearate, zinc stearate, talc, propylene glycol, PEG 4000, PEG 5000, PEG 6000, and stearic acid;

and, wherein the tap density of the compacted composition is at least about 0.6 g/mL.

In a preferred embodiment, the invention further provides is a rapidly dissolving compacted ribavirin composition comprising of:

| Ingredient | mg |
|---|---|
| Ribavirin USP | 150.0 to 250.0 |
| Lactose Monohydrate NF | 30.0 to 50.0 |
| Microcrystalline Cellulose NF | 37.5 to 62.5 |
| Croscarmellose Sodium NF | 4.5 to 7.5 |
| Magnesium Stearate NF | 2.25 to 5.0 | and wherein the tap density of the compacted composition is at least about 0.6 g/mL.

In a preferred embodiment, the invention provides a rapidly dissolving compacted ribavirin composition comprising:

| Ingredient | mg |
|---|---|
| Ribavirin USP | 200.0 |
| Lactose Monohydrate NF | 40.0 |
| Microcrystalline Cellulose NF | 50.0 |
| Croscarmellose Sodium NF | 6.0 |
| Magnesium Stearate NF | 4.0 | wherein the tap density of the compacted composition is at least about 0.6 g/mL;and wherein the ribavirin is substantially free of polymorphic forms of ribavirin.

In another aspect, this invention provides a method of producing a rapidly dissolving compacted ribavirin composition which comprises the steps of:

(a) admixing an antivirally effective amount of ribavirin, an effective amount of a pharmaceutically acceptable disintegrant, and an effective amount of at least one filler for a time sufficient to form a homogeneous mixture;

b) compacting the homogeneous mixture of Step (a) at a compressing force in the range of about 50 to about 75 kN for a time sufficient to produce an acceptable compact wherein the ribavirin is substantially free of polymorphic forms of ribavirin; and c) admixing the acceptable compact of Step (b) with an effective amount of a lubricant for a time sufficient to produce a uniform, rapidly dissolving compacted ribavirin composition.

DETAILED DESCRIPTION OF THE INVENTION

We have surprisingly discovered that we can consistently manufacture a uniform ribavirin composition which consistently meets and exceeds the dissolution specifications which requires that 80% of the ribavirin be dissolved in water in 30 minutes; about 90% of the ribavirin in the compacted ibavirin of the compositions of this invention is consistently dissolved in water in 15 minutes and about 100% of the ribavirin from the compositions of this invention is dissolved in 30 minutes. The disintegration time of the ribavirin compositions of this invention was reduced to less than 10 minutes compared to the Virazole capsule composition which disintegrated in 20 minutes (see Table 1).

The ribavirin composition of this invention was blended and passed through a roller compactor at a compressing force in the range of about 50 to 75 kiloNewtons ("kN") for a time sufficient to produce an acceptable compact. An "acceptable compact" as used herein means a compact that is in the form of a ribbon which is homogeneous, and almost completey free,i.e., more than 95% free, of lamination and flaking, and the ribavirin is substantially free of other polymorphic forms of ribavirin. A compressing force in the range of 50 to about 75 kN consistently produced an acceptable compact. Typically suitable screw speeds and (on the Fitzpatrick roller/compactor) roller speeds include (1) a screw speed of 40 revolutions per minute ("RPM") with a roller-speed of 10 RPM; (2) a screw speed of 30 RPM with a roller speed of 7 RPM; and (3) a screw speed of 22 RPM with a roller speed of 5 RPM. No definitive range of screw speeds and roller speeds was able to be deduced from these results.However we have discovered that an acceptable compact is consistently obtainable by maintaining the compressing force in the range of about 50 to about 75 kN. The compacted material is milled, combined with a lubricant and the resulting tap density of the resulting ribavirin composition is at least 0.6 g/mL and preferably it is significantly higher, e.g., in the range of about 0.75 to about 0.85 g/mL. The compacted ribavirin composition of this invention surprisingly has substantially uniform physical and chemical characteristics and and the ribavirin in the compacted ribavirin composition is substantially free of other polymorphic forms of ribavirin, i.e.,there are no signs of polymorphic change in ribavirin as determined by differential scanning calorimetry. This result is particularly surprising in view of the large amount of heat generated during the compaction step which could normally produce polymorphic forms.

The rapidly dissolving ribavirin composition of this invention is stable and has been subjected to three freeze-thaw cycles without any adverse impact upon the physical apperance, tap density, dissolution or disintegration rates.

Typically suitable disintegrants include pharmaceutically acceptable disintegrants which are chemically and physically compatible with ribavirin; preferably those disintegrants are selected from the group consisting of croscarmellose sodium, sodium starch glycolate, corn starch, pregelatinized starches, sodium carboxymethyl cellulose, potato starch, microcrystalline cellulose, cross-linked polyvinylpyrrolidone, magnesium aluminium silicate, bentonite, alginic acid and alginates.

The effective amount of a disintegrant found useful in the ribavirin compositions of this invention is in the range of about 1.0 to about 3.0 weight percent, preferably about 1.5 to about 2.5 weight percent, and most preferably about 2.0 weight percent of the ribavirin compositions of this invention. The prefered disintegrant is croscarmellose sodium.

Typically suitable lubricants include any pharmaceutically acceptable solid or liquid lubricants which are used to enhance the flow and prevent sticking of the ribavirin composition after compaction and whch are chemically and physically compatible with ribavirin.

Typically suitable lubricants include magnesium stearate, calcium stearate, zinc stearate, talc, propylene glycol,PEG 4000, PEG 5000, PEG 6000, and stearic acid.

The effective amount of a lubricant found useful in the ribavirin compositions of this invention is in the range of about 0.75 to about 2.0 weight percent, preferably about 1.0 to about 1.7 weight percent, and most preferably about 1.3 weight percent of the ribavirin compositions of this invention. The prefered lubricant is magnesium stearate.

Typically suitable fillers include any such pharmaceutically acceptable filler which gives the powder ribavirin composition bulk and which is physically and chemically compatible with ribavirin; preferably those fillers are selected from the group consisting of lactose anhydrous, lactose monohydrate, sucrose, mannitol, microcrystalline cellulose, pregelatinized starches, dibasic calcium phosphate dihydrate,calcium sulfate trihydrate and calcium sulfate dihydrate.

Typically two fillers are used in the ribavirin compositions of this invention. The effective amount of the fillers found useful in the ribavirin compositions of this invention is in the range of about 20 to about 40 weight percent, preferably about 25 to about 35 weight percent, and most preferably about 30 weight percent of the ribavirin compositions of this invention. One of the prefered fillers is lactose monohydrate which is typically present in the range of about 10 to about 15 weight percent, more preferably about 13 to about 14 weight percent of the ribavirin compositions of this invention. The other prefered filler is microcrystalline cellulose which is typically present in the range of about 10 to about 20 weight percent, more preferably about 12 to about 18 weight percent, and most preferably about 16 to about 17 weight percent of the ribavirin compositions of this invention.

The term "tap density" as used herein means the measured mass of a powder attained at a limiting volume measured in a cylinder after being "tapped down", typically by a mechanical device; typically tap density is recorded as mass in grams divided by volume in milliliters("mL"). The tap density is measured in accordance with the procedure described in USP 23, NF 18, Supplement 6,(1997), procedure <616> at page 3768. The tap density of the orally administrable ribavirin composition of this invention is at least 0.6 g/mL which is advantageous when a capsule containing 200 mg of ribavirin in the 300 mg preferred composition of this invention is used.

Typically the tap densities of the orally administrable ribavirin is in the range of about 0.75 g/mL to about 0.85 g/mL.

While the rapidly dissolving ribavirin compositions of this invention are described for 200 mg ribavirin strengths, other strengths e.g., 300 or 400 mg of ribavirin, may be used without deviating from this invention.

Ribavirin (1000–1200 mg in divided daily doses such as 600 mg BID) is being used in clinical trials in combination with subcutaneous injections of interferon alfa-2b (3 million international units, three times a week (TIW)) to treat chronic hepatitis C patients. Thus, the term antivirally effective amount of ribavirin as used herein means dosages of ribavirin, e.g.,200 mg, 300 mg or 400 mg, which would provide the 1000–1200 mg/day of ribavirin used to treat chronic hepatitis C patients in combination with the interferon alfa-2b.

Manufacturing Procedure

General Manufacturing Procedure (1) Charge the ribavirin, one or more fillers and disintegrant into a suitable double cone blender.

(2) Blend the charge from step (1) for a time sufficient to form uiniform blend.

(3) Optionally pass the blend of step (2)-if the such blend should contain lumps- through a suitable comminutor mill set at medium speed to provide a lump-free blend.

(4) Pass the milled uniform blend in step 2 or 3 through a suitable roller/compactor equipped with an oscillator for screening and operated at a compressing force of about 50 to about 70 kN for a time sufficient to produce an acceptable compact;

(5) Combine the compacted screened blend in step (4) and charge said blend to the blender used in step (1).

(6) Charge the lubricant to the blend in step (5) and blend the mixture for a time sufficient to produce a uniform mixture;

(7) Fill the uniform mixture in step (6) into capsules.

A large scale batch of the capsule formulation was prepared using the formulations of Example 1 or 2.

Procedure:

1. Charge the ribavirin, microcrystalline cellulose, lactose monohydrate, and croscarmellose sodium into a suitable double cone blender of appropriate volume.
2. Blend the charge in step (1) for 10 to 15 minutes, preferably about 15 minutes. Discharge the so-formed mixture into plastic lined containers". 3. Optionally pass the blended mixture from step (2) through a suitable comminutor mill set at medium speed, impact hammers forward fitted with a No. 6 mesh screen. (This step is optional and may be eliminated if the blended mixture from step (2) is lump-free.)
4. Pass the milled blend in step 2 or 3 through a suitable roller/compactor such as a Bepex or Fitzpatrick roller compactor machine equipped with an oscillator for screening. Operate the roller compactor at a compressing force of about 50 to about 75 kN for a time sufficient to produce an acceptable compact. (An acceptable compact is normally produced with a single pass of the milled blend from step (3) through the compactor. The compacted material is thereafter directly fed into the oscillating mill equipped with a 16 mesh screen.)
5. Combine the compacted, screened blend in step 4 and charge the blend to the blender used in Step 1. Blend for 10 minutes. Remove samples of the blend for tap density and sieve analysis testing.
6. Charge the magnesium stearate to the blend in step 5 and blend for about 3 minutes or a time sufficient to produce a uniform mixture.
7. Fill the uniform mixture from Step 6 into No. 1 white opaque, two-piece hard gelatin capsules using an appropriate high speed capsule filling equipment, e.g., a Zanasi AZ40 or H&K 1500.
8. Polish and dedust the filled capsules using a rotating brush capsule polishing machine, e.g., Key Turbo-Kleen CP-300 equipped with an empty capsule eliminator.
   a. Analyze the blended mixture in step(2) for blend uniformity. Based on this analysis, it was then determined that a blending time of 10 to 15 minutes was sufficient to produce an acceptable blend uniformity.

Ribavirin is mutagenic and teratogenic and appropriate precautions must be taken to ensure the safety of the manufacturing personnel.

The following examples illustrate, but do not limit, the present invention:

EXAMPLE 1

The above-described manufacturing procedure may be used to blend, compact, and mill the following compositions:

| Ingredient | mg |
| --- | --- |
| Ribavirin USP | 150.0 to 250.0 |
| Lactose Monohydrate NF | 30.0 to 50.0 |
| Microcrystalline Cellulose NF | 37.5 to 62.5 |
| Croscarmellose Sodium NF | 4.5 to 7.5 |
| Magnesium Stearate NF | 2.25 to 5.0 |

The above compositions have tap densities of at least 0.6 g/mL.

EXAMPLE 2

The procedure of Example 1 was followed to prepare the following composition:

| Ingredient | mg |
| --- | --- |
| Ribavirin USP | 200.0 |
| Lactose Monohydrate NF | 40.0 |
| Microcrystalline Cellulose NF | 50.0 |
| Croscarmellose Sodium NF | 6.0 |
| Magnesium Stearate NF | 4.0 |

The tap density was 0.77 g/mL.

(1) Preferably the lactose monohydrate NF is spray dried. The composition was filled into capsules and the following dissolution results were recorded:

| Dissolved Time (minutes) | AverageWeight % of Ribavirin Dissolved | (Weight %)Ribavirin (Range) |
| --- | --- | --- |
| 15 | 99 | (93–103) |
| 30 | 101 | (98–103) |
| 45 | 101 | (98–104) |
| 60 | 102 | (99–104) |

12 capsules of the formulation of Example 2 were tested using a USP basket at 100 RPM in 900 mL of distilled water operated in accordance with the procedure described in USP 23, NF-18 procedure <711>.

The formulation of Example 2 exhibited no signs of polymorphic changes in the ribavirin as determined by differential scanning calorimetry. USP 23, NF-18 Supplement 6, procedure <891>, 1997.

The disintegration time for the formulation of Example 2 was measured as described in Table 1; the capsules disintegrated in 7–9 minutes.

The effect of freeze-thaw cycling was determined for the formulation of Example 2 in capsules. The capsules were subjected to three freeze-thaw cycles. The first two freeze and thaw cycles lasted 24 hours. The last freeze-thaw cycle was 72 hours followed by 24 hours at ambient—i.e. room temperatures.

Physical observation, disintegration, and dissolution studies were performed. No significant change in physical appearance the disintegration time or dissolution rates were observed compared to the initial test results.

| Time (minutes) | Avg.Weight % Ribavirin Dissolved for a capsule | Wgt % Ribavirin Dissolved (Range) |
| --- | --- | --- |
| 15 | 93 | (84–100) |
| 30 | 96 | (89–100) |
| 45 | 96 | (86–101) |
| 60 | 96 | (86–101) |

Essentially no changes were observed in the tap density, dissolution or disintegration rates of the ribavirin composition of Example 2.

EXAMPLE 3

The following composition represents the composition of a typical Virazole 200 mg capsule (uncompacted):

| Ingredient | mg |
| --- | --- |
| Ribavirin USP | 200.0 |
| Lactose Monohydrate NF Spray Dried | 46.0 |
| Microcrystalline Cellulose NF | 50.0 |
| Magnesium Stearate NF | 4.0 |
| Capsule Fill Weight | 300.0 |
| Capsule Size | No. 1 |
| Capsule Type | White Opaque |

TABLE 1

Comparative dissolution and disintegration results for the rapidly dissolving ribavirin composition of Examples 2 and 3:

A. Dissolution

| | Weight % Ribavirin Dissolved | |
| --- | --- | --- |
| Time | Compacted Ribavirin[1] | Virazole Composition[2] |
| 15 | 91 | 84 |
| 30 | 98 | 96 |
| 45 | 99 | |
| 60 | 99 | |

B. Disintegration[3]

| Product | Disintegration Time (minutes) |
| --- | --- |
| Compacted ribavirin composition of Example 2 of this invention | 6–8 |
| Virazole composition of Example 3 | ~20 |

[1] 12 capsules of Example 2 were tested using a USP basket at 100 RPM in 900 mL of distilled water operated in accordance with the procedure described in USP 23, NF18, procedure <711> ,1995.
[2] The uncompacted Virazole composition of Example 3 was used.
[3] 6 capsules were tested in an USP apparatus operated in accordance with the procedure described in USP 23, NF 18 procedure <701>.,1995

What is claimed is:

1. A method of producing a rapidly dissolving compacted ribavirin composition which comprises the steps of:

(a) admixing an antivirally effective amount of ribavirin, an effective amount of a pharmaceutically acceptable disintegrant, and an effective amount of at least one filler for a time sufficient and at a temperature wherein the heat produced is insufficient; and to form a homogeneous mixture;

b) compacting the homogeneous mixture of Step (a) at a compressing force in the range of about 50 to about 75 kN for a time sufficient to produce an acceptable compact wherein the ribavirin is substantially free of polymorphic forms of ribavirin;

c) admixing the acceptable compact of Step (b) with an effective amount of a lubricant for a time sufficient to produce a uniform, rapidly dissolving compacted ribavirin composition having a uniformly high tap density of at least about 0.60 glmL and wherein 80% of the rapidly dissolving compacted ribavirin composition dissolves in water in about 30 minutes.

2. The method of claim 1 wherein the rapidly dissolving compacted ribavirin has a tap density in the range of about 0.75 g/mL to about .0.85 g/mL.

3. The method of claim 1 wherein more than about 90% of the rapidly dissolving compacted ribavirin composition dissolves in water in about 15 minutes.

4. The product produced by the method of claim 1.

5. The method of claim 1 wherein at least one filler is selected from the group consisting of lactose anhydrous, lactose monohydrate, sucrose, mannitol, microcrystalline cellulose, pregelatinized starches, dibasic calcium phosphate dihydrate,calcium sulfate dihydrate and calcium sulfate trihydrate.

6. The method of claim 1 wherein one of the fillers is lactose monohydrate.

7. The method of claim 1 wherein the other fillers is microcrystalline cellulose.

8. The method of claim 1 wherein the disintegrant is selected from the group consisting of croscarmellose sodium, sodium starch glycolate, corn starch, pregelatinized starch, sodium carboxymethyl cellulose, potato starch, microcrystalline cellulose, cross-linked polyvinylpyrrolidone, magnesium aluminium silicate, bentonite, alginic acid and alginates.

9. The method of claim 1 wherein the disintegrant is croscarmellose sodium.

10. The method of claim 1 wherein the lubricant is selected from the group consisting of magnesium stearate, calcium stearate, zinc stearate, talc, propylene glycol, PEG 4000, PEG 5000, PEG 6000, and stearic acid.

11. The method of claim 1 wherein the lubricant is magnesium stearate.

* * * * *